United States Patent [19]

Lane et al.

[11] Patent Number: 5,494,029
[45] Date of Patent: Feb. 27, 1996

[54] LARYNGEAL STENTS

[75] Inventors: Charles Lane, Duxbury, Mass.; Isaac Elaicher, Pepper Pike, Ohio; Lewis H. Marten, Westwood, Mass.

[73] Assignee: Hood Laboratories, Pembroke, Mass.

[21] Appl. No.: 264,411

[22] Filed: Jun. 23, 1994

Related U.S. Application Data

[63] Continuation of Ser. No. 953,514, Sep. 29, 1992, abandoned.

[51] Int. Cl.$^6$ .................. A61M 16/00; A61M 29/00; A62B 9/06; A61F 2/20
[52] U.S. Cl. .................. 128/207.15; 623/9; 606/192; 128/207.16; 604/96; 604/101
[58] Field of Search .................. 128/207.14–207.16; 600/31; 623/9; 604/41, 42, 96, 101, 104, 278; 606/192; 607/72, 134

[56] References Cited

U.S. PATENT DOCUMENTS

| | | | |
|---|---|---|---|
| D. 295,557 | 5/1988 | Barber et al. | 623/9 |
| 3,211,152 | 10/1965 | Stern | 128/207.15 |
| 3,481,339 | 12/1969 | Puig | 128/207.15 |
| 3,640,282 | 2/1972 | Kamen et al. | 128/207.15 |
| 3,769,983 | 11/1973 | Merav | 128/207.15 |
| 3,995,643 | 12/1976 | Merav | 128/207.15 |
| 4,018,231 | 4/1977 | Wallace | 128/207.15 |
| 4,091,816 | 5/1978 | Elam | 128/207.15 |
| 4,141,364 | 2/1979 | Schultze | 128/207.15 |
| 4,166,468 | 9/1979 | Haynie | 128/207.15 |
| 4,274,162 | 6/1981 | Joy et al. | 623/9 |
| 4,417,576 | 11/1983 | Baran | 128/207.15 |
| 4,509,514 | 4/1985 | Brain | 128/207.15 |
| 4,586,505 | 5/1986 | Sisson et al. | 606/192 |
| 4,791,923 | 12/1988 | Shapiro | 128/207.15 |
| 4,794,924 | 1/1989 | Eliachar | 623/9 |
| 4,995,388 | 2/1991 | Brain | 128/207.15 |

OTHER PUBLICATIONS

Cardiopulmonary Anatomy and Physiology, des Jardins (ed.). Delmar Publishers, Inc., 1988, ISBN #0827328362, pp. i, ii, 6.

*Primary Examiner*—Kimberly L. Asher
*Attorney, Agent, or Firm*—Kane, Dalsimer, Sullivan, Kurucz, Levy, Eisele and Richard

[57] ABSTRACT

A laryngeal stent for supporting anatomical features of the mammalian larynx, including a human larynx is formed by a gas-inflatable envelope fabricated from a resilient, deformable material can conform to the anatomical surfaces of the larynx within the mammal's esophagus when pressurized by the gas. In preferred embodiment stents, the surface of the envelope is coarse, allowing for the venting of air between the laryngeal surfaces and the envelope. However, the stent conforms so closely to the anatomical features of the larynx that sutures are not required to anchor the stent in place.

8 Claims, 4 Drawing Sheets

/ 1

LARYNGEAL STENTS

This application is a continuation of application Ser. No. 07/953,514, filed Sep. 29, 1992, now abandoned.

BACKGROUND OF THE INVENTION

1. Field of the Invention

The invention relates to surgical appliances and more particularly to laryngeal stents for use in a mammal, including a human.

2. Brief Description of the Prior Art

Laryngeal stents are appliances inserted into the larynx of a mammal for support of the larynx structure during a period of healing, for example following surgery. Early laryngeal stents were relatively rigid, solid devices sculpted to mate with anatomical features of the larynx. Sutured in place, the stents were often sources of tissue irritation, causing degrees of trauma, edema and local discomfort. These early stents also blocked the normal airway, requiring the ancillary presence of a tracheotomy. Should the tracheotomy become restricted by mucous or the like, the laryngeal stent blockage could become critical, giving rise to great discomfort and further trauma to the larynx as the stent is moved in response to the mammal's reflex to a lack of air.

An important improvement in the art occurred with development of the Eliachar laryngeal stent (U.S. Pat. No. 4,794,924 issued Jan. 3, 1989). This improved stent provided a relatively rigid, hollow tube to replace the earlier solid body of the stent. A valve at one end of the stent provided air communication through the hollow tube, when high pressure build up below the stent required venting (for example as occurs when the patient coughed). Although the stent body was still relatively rigid, the tube walls were more resilient than a solid stent, permitting some degree of conformation with the larynx anatomy. However, a given device, represented a compromise of desired physical features. For example, if the stent was manufactured with very thin, very flexible hollow bodies, it would exert little pressure on larynx tissues with consequent reductions in irritation. However, this may sacrifice physical support for immobilizing larynx structures. On the other hand, if the hollow body walls are manufactured with greater thickness, the desired flexibility and resilience is sacrificed to achieve the support objective. The surgeon has therefore been faced with a need to select from an inventory of different stents, to satisfy the variety of individual patient needs.

The laryngeal stents of the present invention are a further advance in the art, allowing one to control both surface resilience and support structure provided by the stent. Anchoring of the stent within the larynx is facilitated, without the need for suturing to the patient's tissue. Other advantages associated with the laryngeal stents of the invention will be described hereinafter in relation to particular embodiment stents.

SUMMARY OF THE INVENTION

The invention comprises a laryngeal stent, which comprises;

(A) an elongate, generally tubular, deformable, gas-impermeable, inflatable envelope having when inflated;

(i) an enlarged upper portion of a dimension and configuration for positioning in a mammalian larynx to support anatomical features in the glottic and supraglottic region of said larynx;

(ii) a tapered lower portion of a dimension and configuration for positioning in a mammalian larynx to support anatomical features in the subglottic region of said larynx;

(iii) an outer surface of resilient, deformable material able to substantially conform to the anatomical surface of the larynx;

(iv) a first closed end at the upper portion of the envelope;

(v) a second closed end at the lower portion of the envelope;

(vi) an interior closed chamber defined by the envelope together with the closed first and second ends; and (B) means for inflating the envelope and maintaining said inflation, in fluid communication with the interior closed chamber.

DETAILED DESCRIPTION OF THE PREFERRED EMBODIMENTS OF THE INVENTION

Those skilled in the art will gain an appreciation of the invention from a reading of the following description of preferred embodiments, when viewed in conjunction with the accompanying drawings of FIGS. 1–7, inclusive.

Figure 1:
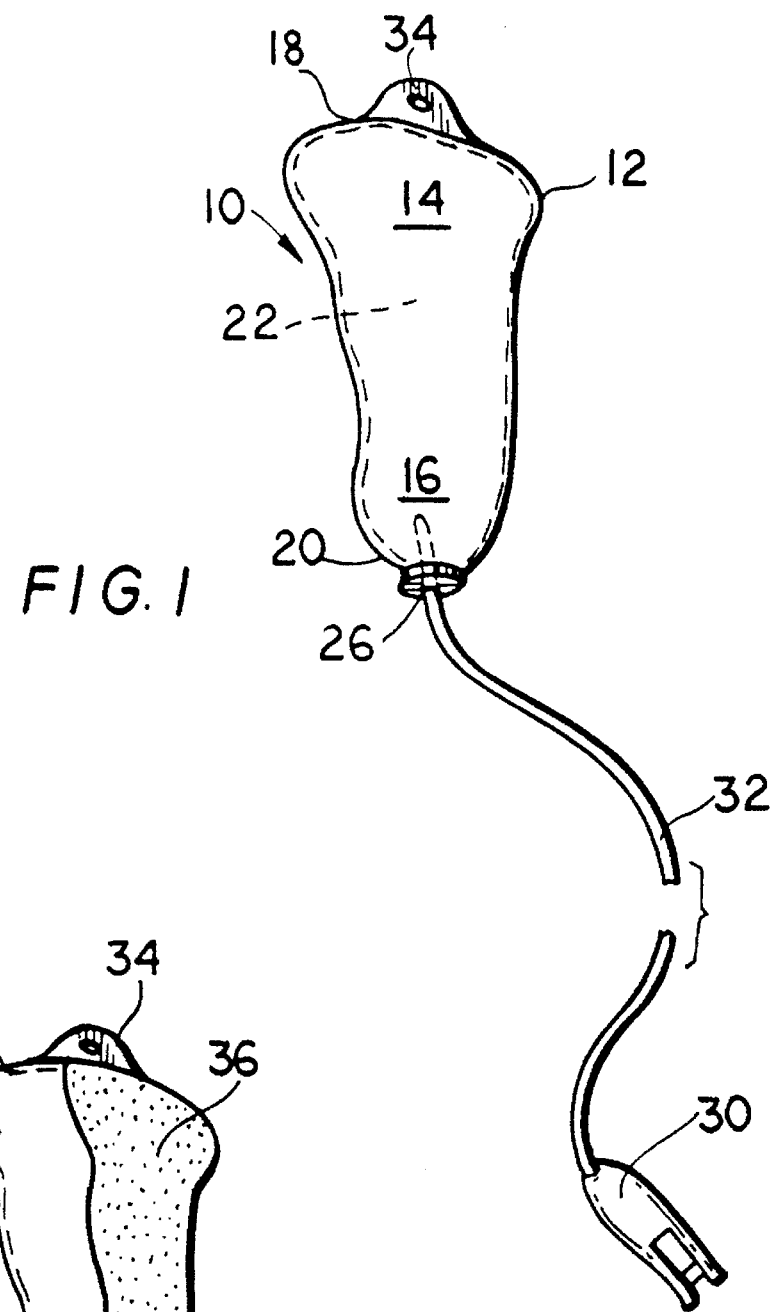
FIG. 1 is a view-in-perspective of an embodiment laryngeal stent of the invention.

Referring first to FIG. 1, there is seen a view-in-perspective of a preferred embodiment laryngeal stent 10 of the invention. The stent 10 comprises an inflatable, flexible envelope 12, which is a generally elongate tube of a deformable, gas-impermeable material such as a film of a medical grade [Food and Drug Administration (FDA) approved] synthetic polymeric resin. The envelope 12 has an enlarged upper portion 14 of a dimension and configuration for positioning adjacent a mammalian larynx to contact and support anatomical features in the glottic and supraglottic region of the larynx. The width or diameter of portion 14 is such as to provide a seal above the larynx to prevent aspiration. A tapered lower portion 16 is of a smaller dimension and configuration for positioning in the larynx to contact and support anatomical features in the subglottic region of the larynx. The ends 18, 20 of the envelope 12 are closed, to define with the envelope 12 a closed interior chamber 22. The outer surface 24 of the inflated envelope 12 is resilient, soft and deformable, permitting it to substantially conform to the anatomical surface of the larynx as exposed within the trachea. The chamber 22 of stent 10 as shown in the FIG. 1 is air-filled to inflate the envelope 12. Inflation may be carried out by inserting a cannula (not shown in FIG. 1) through a self-sealing (elastomer covered) portal 26 in the end 20 of the envelope, connected with a pump (syringe) suitable for moving air under pressure into the chamber 22. After inflation to a desired pressure, the cannula and pump may be disconnected without significant loss of air pressure within the chamber 22. The degree of inflation may be adjusted to soften or rigidify the outer surface 24 of the envelope 12, thereby adjusting the support contact provided to the larynx by the stent 10. Advantageously, the air pressure and volume of air within chamber 22 is reduced during insertion and removal of the stent 10 into and out of the laryngeal zone within the trachea to allow for ease and facilitation of insertion and withdrawal with minimum disruption to laryngeal tissues. Insertion and withdrawal may be through a tracheotomy opening below the larynx. After installation of stent 10 and inflation to a desired pressure, pressure relief valve 30, which is in fluid communication with chamber 22 through flexible conduit 32, prevents extreme pressure increases within the chamber 22 which might arise from muscle constriction or like conditions. Alternatively, valve 30 may be a pressure responsive valve permitting re-inflation of chamber 22 if there is a pressure loss and functions then to maintain inflation of the envelope 12.

Preferred as the gas-impermeable material for fabricating gas-impermeable envelopes 12 for use in the stents 10 of the invention are films of elastomeric block copolymers characterized by an A-B-A' structure, wherein A and A' are polymerized vinyl aromatic hydrocarbon blocks, and B is an ethylene-butylene block derived from at least one polymerized conjugated diene. In preferred embodiments, the block copolymers preferably contain between about 15% and 50% by weight of vinyl aromatics.

Center block B of the block copolymer should be almost completely hydrogenated, i.e., the average unsaturation of the copolymer should be reduced to less than about 20% of its original value. In more preferred embodiments, the average unsaturation will be reduced to less than 10% and most preferably, less than about 5% of its original value. Methods for accomplishing the hydrogenation of the B block are known in the art.

In preferred embodiments of this invention, A and A' are polymers independently derived from the group of monomers consisting of styrene, alpha-methyl styrene, paramethyl styrene, vinyl toluene, vinyl xylene, vinyl naphthalene, chlorostyrene, bromostyrene, dibromstyrene, and combinations thereof. Styrene monomer is most preferred.

In the preferred embodiments, center block B is derived from at least one conjugated diene such as 1,3-butadiene. In the most preferred embodiments, B is obtained via post-hydrogenation of polybutadiene.

It is advantageous that the polymers corresponding to each block of the block copolymer used in this invention be within a certain molecular weight range. Thus, the A and A' blocks may have a weight average molecular weight (independently) in the range of about 4,000 to about 15,000, and preferably, in the range of about 7,000 to about 8,000. The weight average molecular weight of the B block may be in the range of about 25,000 to about 90,000 and preferably, in the range of about 30,000 to about 40,000.

The preparation of elastomeric block copolymers such as the type used in fabricating envelope 12 of the present invention, is known in the art. For example, one technique involves the successive polymerization of the monomers in solution in the presence of a monolithium hydrocarbon initiator. Further aspects of the preparation of these polymers can be found in European Patent 0,095,098; in U.S. Pat. Nos. 3,113,986; 3,431,323; 3,700,633; and 4,167,507; the contents of all of these references being incorporated herein by reference.

An especially preferred elastomeric block copolymer for use as an ingredient in the polymer compositions to fabricate envelopes 12 of this invention comprise blocks of styrene and post-hydrogenated polybutadiene within the above-prescribed molecular weight ranges, and is often referred to as "SEBS". Block copolymers of this type are commercially available from Shell Chemical Company under the trademark KRATON™, and include KRATON™ D1101, G1650, G1651, G1652 and G1702.

The envelope 12 may also be rendered radio-opaque by compounding the polymeric resin employed with a metal salt.

The envelope 12 may be fabricated by the well-known technique of plastisol dipping and may be carried out to vary the envelope 12 thickness in selected areas, so as to obtain envelopes 12 with varied rigidity in the selected area (soft or hard) as desired to support specific anatomical features of the larynx. An average thickness of envelope 12 may be within the range of from about 0.010 to about 0.012 inches as an example. Also, the envelope 12 may be fabricated with integral inserts, tabs and the like to facilitate insertion and removal from the trachea. As shown in FIG. 1, an apertured tab 34 is such an integral component of stent 10, useful to anchor the stent 10 in place.

Figure 2:
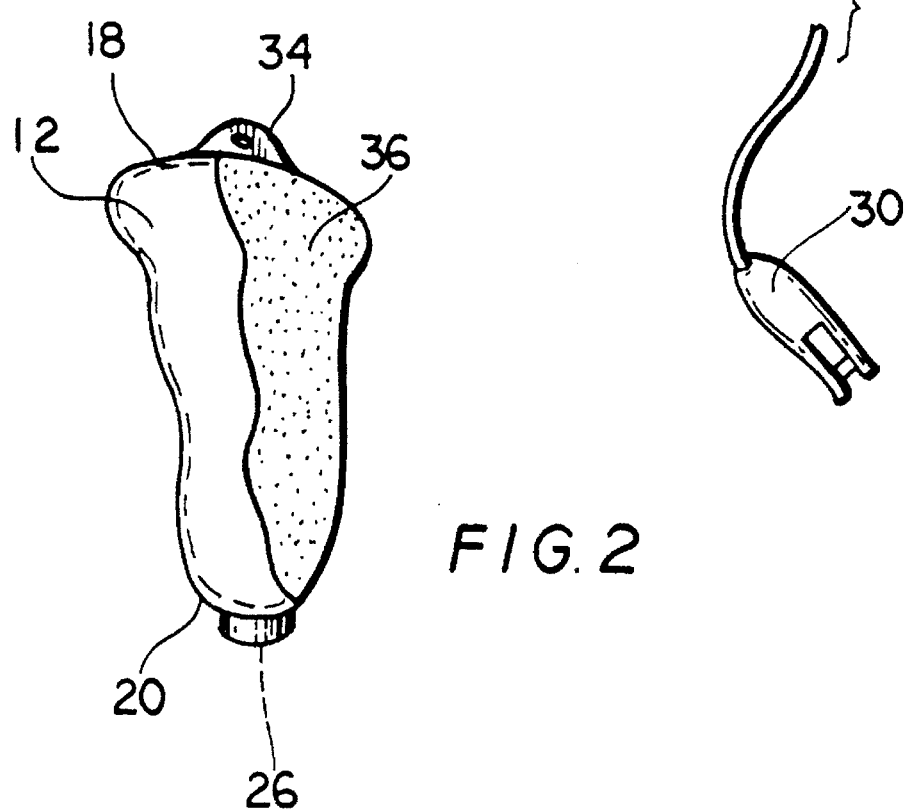
FIG. 2 is a view of a partially cut-away alternate envelope component for use in the stent of FIG. 1.

FIG. 2 is a view of a partially cut-away alternate envelope component for use in the stent 10 of FIG. 1. In the alternate envelope component shown in FIG. 2, components similar to those shown in FIG. 1 are similarly numbered. In essence, the alternate embodiment of FIG. 2 is an envelope as shown in FIG. 1, wherein the chamber 22 is filled with an open cell, synthetic polymeric resin foam 36 means for inflating and maintaining inflation and a constant volume within chamber 22. This alternate embodiment stent 10 of the invention provides for low pressure and minimal possibility of over-inflation. The volume of the chamber 22 in the stent may be decreased during insertion by squeezing the stent to express air normally found in the open cell foam 36 structure. Upon release, the foam 36 will return the chamber 22 to its original volume by a flow of air back into the foam 36 structure. Similarly, the volume chamber 22 of the stent 10 may be decreased during removal by squeezing the air from the open cell foam 36. This permits and facilitates removal of the stent 10 with minimal disruption to adjacent body tissues. The foam 36 within the stent of FIG. 2 is a resilient mass, sponge-like in character and having a multitude of interstices spread therethrough. Representative of such foam materials are those prepared by foaming a polyurethane or like synthetic plastic resin material which is FDA approved.

Figure 3:
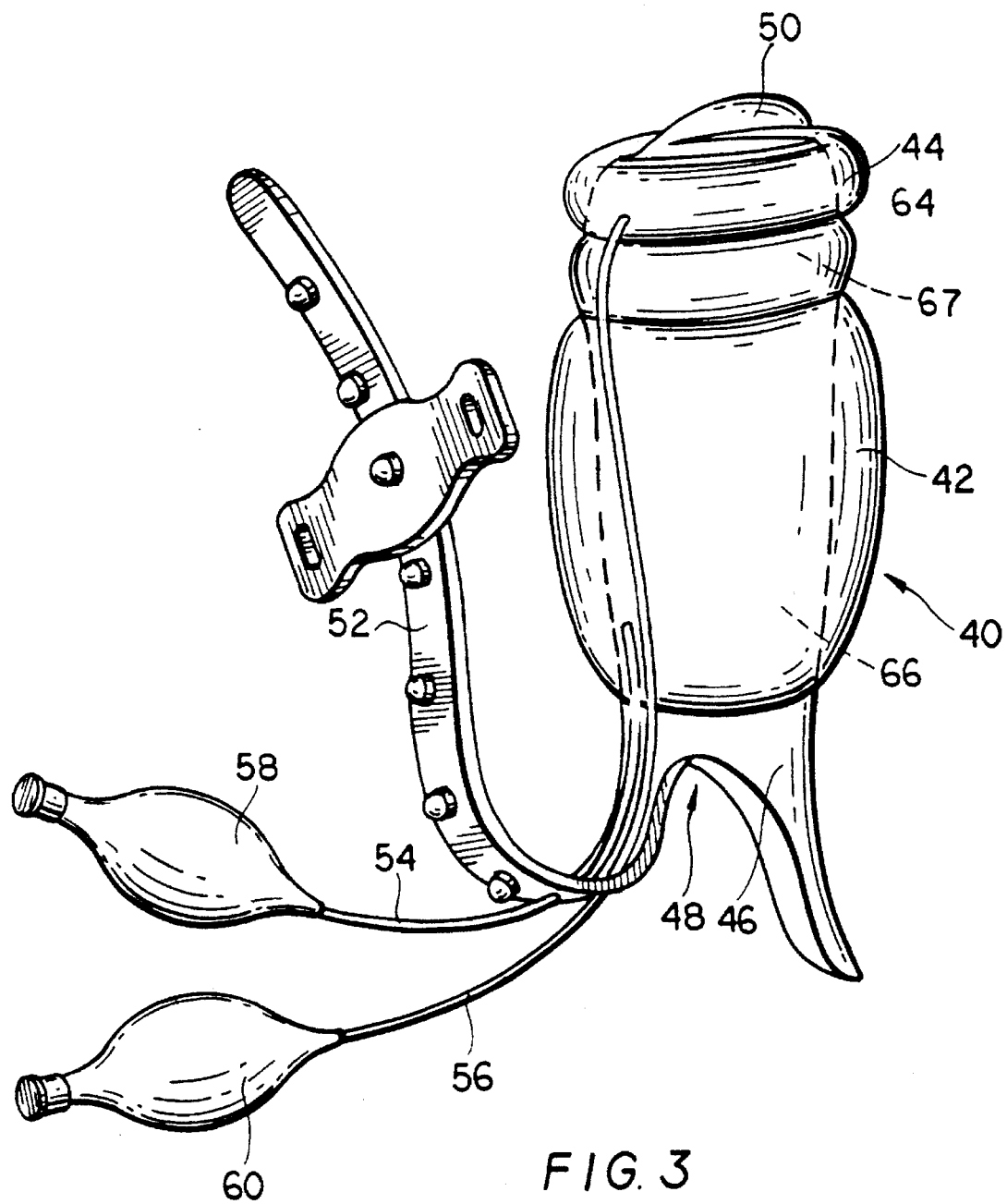
FIG. 3 is a view-in-perspective of another embodiment laryngeal stent of the invention.

FIG. 3 is a view-in-perspective of still another embodiment laryngeal stent of the invention. The stent 40 shown in FIG. 3 comprises a plurality of separate envelopes 42, 44 which are fabricated from the same materials employed to fabricate the envelope 12 previously described. Each of the envelopes 42, 44 are closed at both upper and lower ends by their mounting upon a supporting hollow tube 46. The hollow tube 46 does not engage with anatomical features of the larynx during use of the stent 40. Instead, the soft, pliant, elastic envelopes 42, 44 perform the support function for anatomical features of the larynx. The tube 46 is hollow, providing an open lumen 48 closed at the upper end by a one-way pressure-relief valve 50. The open lumen 48 permits the passage of air in order to enable excess pressures from beneath the stent 40 to be released, and to facilitate speech under certain circumstances described below. The envelopes 42, 44 are spaced from each other on the support tube 46 to permit space 67 for the vocal cords when the stent 40 is emplaced, with this arrangement, speech is possible. A leash 52 may be threaded through the opening of a tracheotomy, to permit anchoring and attachment of the stent 40 to the exterior of the patient's neck at the tracheotomy site. Each of the envelopes 42, 44 is separately connected to respective conduits 54, 56, each of which terminates by connection to a bulb syringe 58, 60 for inflation and maintenance of the interior chambers 64, 66 of each envelope 42, 44. The chambers 64, 66 are each structured to lie between the outer surface of the respective envelopes 42, 44 and the surface of supporting tube 46. The multiple and separate envelopes provided by stent 40 allow further inflation control in specific sites when positioned within the trachea. The separate envelopes 64, 66 allow for supporting sites in varied sections or zones of the larynx. In other respects, the stent 40 is employed in the same manner as stent 10 previously described.

Figure 4:
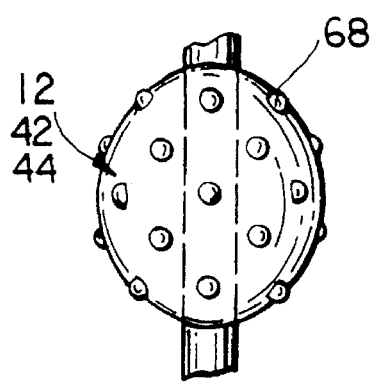
FIGS. 4–6, inclusive, are side elevations of envelope components of the stents of the invention showing some alternative envelope outer surface textures.
Figure 5:
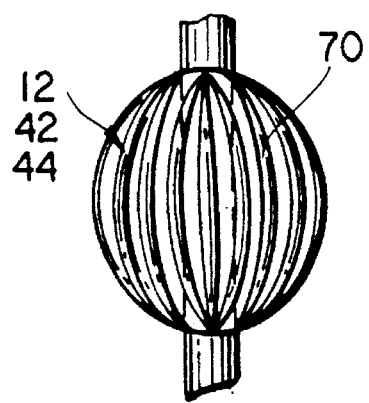
Figure 6:
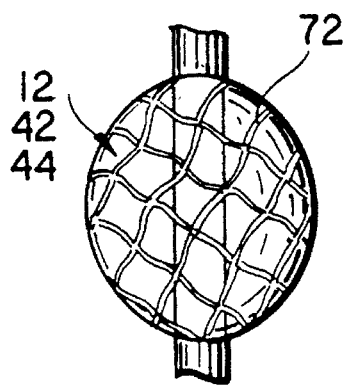

FIGS. 4–6, inclusive, are each side elevations of envelope 12 or 42, 44 components of the stents of the invention shown in FIGS. 1–3, inclusive. As shown in FIGS. 4–6, the outer surface textures of the envelopes 12, 42, 44, are advantageously provided with a plurality of raised points or bumps 68 (FIG. 4), ridges 70 (FIG. 5) or an otherwise course texture 72 (as shown in FIG. 6). Surface characteristics, apart from being smooth, allow for a more positive anchoring of the stent within the zones of the larynx by providing frictional engagement therewith. In addition, a coarse surface provides air channels to by-pass the stent. In the case of stent 40, this permits a small flow of air to by-pass envelope 42, the space 67 and envelope 44. In flowing through the space 67, some speech is enabled, generally sufficient to allow a patient to be understood when speaking.

Figure 7:
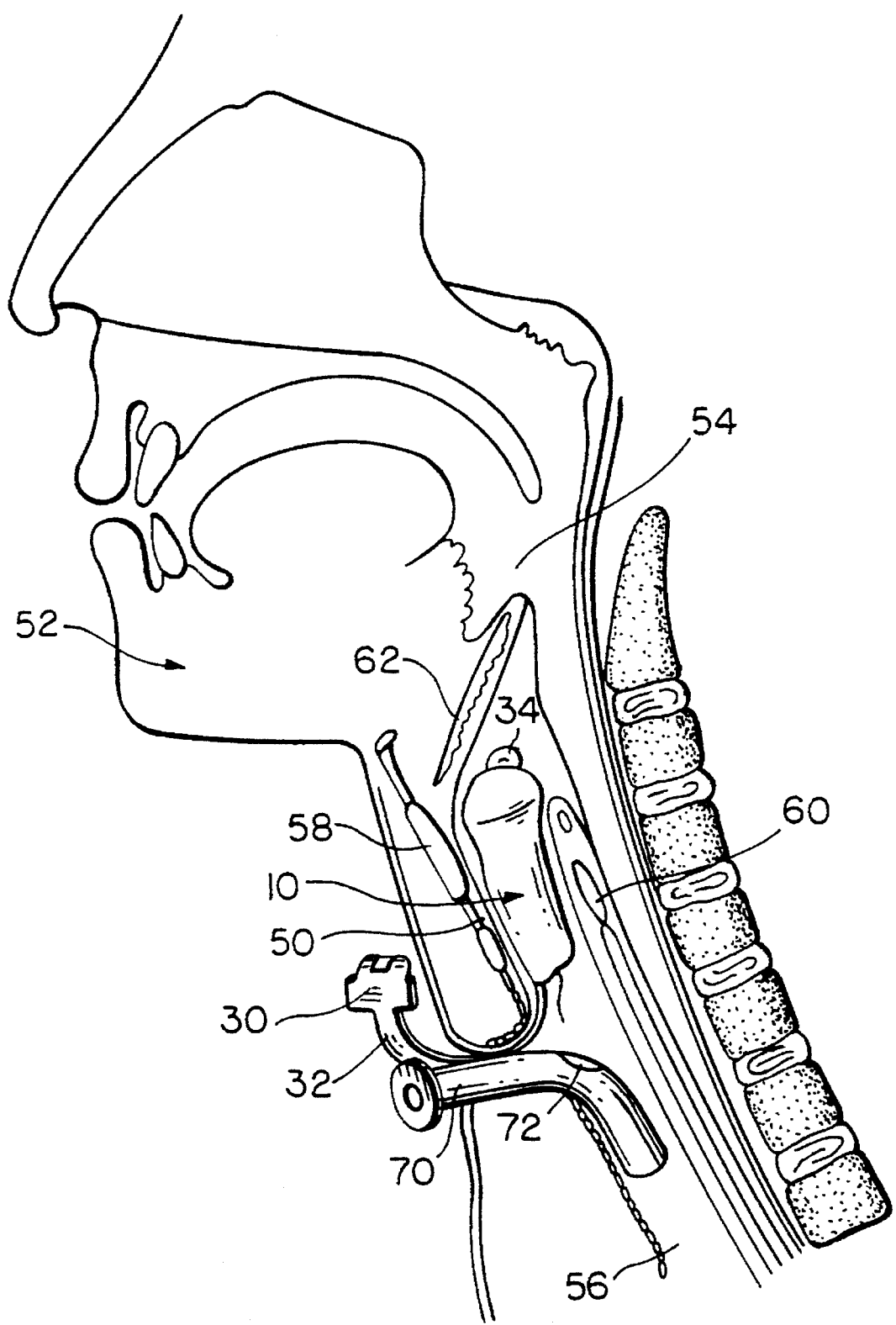
FIG. 7 is a partially schematic view of a laryngeal stent of the invention installed within the larynx of a patient.

FIG. 7 is a sectional, partially schematic view of the laryngeal stent 10 of the invention installed in the larynx 50 of a patient designated by the numeral 52. The larynx 50 is located beneath the pharynx 54 and above the trachea 56. The trachea 56 is comprised of three single cartilages, which are shown in section in FIG. 1, the thyroid 58, the cricoid 60 and the epiglottis 62. The thyroid 58 which is the largest of these cartilages forms the interior part of the larynx and is shaped somewhat like the covers of an open book with the back of the book forming the prominent projection in the anterior neck (Adam's apple). The cricoid cartilage 60 is shaped like a signet ring, with the signet part posterior and the band anterior. The epiglottis 62 is a leaf-like cartilage. The vocal ligaments or cords (not shown) which are comprised of soft tissue covered by mucosa, extend from the thyroid 58 to arytenoid cartilages (not shown) which articulate with the cricoid 60 to move the vocal cords. FIG. 7 shows stent 10 used in conjunction with a conventionally known curved tracheotomy tube 70. Tube 70 is inserted into the trachea through an artificial opening 72 through the patient's neck and the wall of the trachea. Tracheotomy tube 70 is generally curved for easy insertion into trachea 56 and includes an aperture 72 located along the upper side thereof, which aperture 72 provides a passage from the lungs to the larynx.

What is claimed is:

1. A laryngeal stent, which comprises;
   (A) an elongate, generally tubular, deformable, gas-impermeable, inflatable first envelope having when inflated
      (i) a dimension and configuration for positioning in a mammalian larynx to support anatomical features in the glottic and supraglottic region of said larynx;
      (ii) an outer surface of resilient, deformable material able to substantially conform to the anatomical surface of the glottic and supraglottic region of the larynx;
      (iii) a first closed end at the upper portion of the envelope;
      (iv) a second closed end at the lower portion of the envelope;
      (v) an interior closed chamber defined by the envelope together with the closed first and second ends; and
      (vi) means for inflating the envelope and maintaining said inflation, in fluid communication with the interior closed chamber;
   (B) an elongate, generally tubular, deformable, gas-impermeable, inflatable second envelope having when inflated
      (i) a dimension and configuration for positioning in a mammalian larynx to support anatomical features in the glottic and supraglottic region of said larynx;
      (ii) an outer surface of resilient, deformable material able to substantially conform to the anatomical surface of the subglottic region of the larynx;
      (iii) a first closed end at the upper portion of the second envelope;
      (iv) a second closed end at the lower portion of the second envelope;
      (v) an interior closed chamber defined by the second envelope together with the second envelope closed first and second ends; and
      (vi) means for inflating the second envelope and maintaining said inflation, in fluid communication with the interior closed chamber of the second envelope; said first and second envelopes being mounted on the exterior of a hollow tube, in a spaced apart relationship.

2. The stent of claim 1 wherein the means for inflating the first envelope and maintaining said inflation comprises a conduit controlled with a pressure responsive valve.

3. The stent of claim 1 wherein the means for inflating the first envelope and maintaining said inflation comprises an open-cell polymeric resin foam within the interior closed chamber.

4. The stent of claim 1 wherein the outer surface of the first envelope is smooth.

5. The stent of claim 1 wherein the outer surface of the first envelope is frictional.

6. The stent of claim 1 wherein the outer surface of the first and second envelopes bears a plurality of bumps.

7. The stent of claim 1 wherein the outer surface of the first and second envelopes bears a plurality of bars.

8. The stent of claim 1 wherein the outer surface of the first and second envelopes provides air passage when the stent is emplaced in a larynx.

* * * * *